United States Patent
Kim et al.

(10) Patent No.: US 8,895,784 B2
(45) Date of Patent: Nov. 25, 2014

(54) CATALYST FOR REDUCTIVE AMINATION-REACTION AND USES THEREOF

(71) Applicant: Lotte Chemical Corporation, Seoul (KR)

(72) Inventors: Kyung-Jun Kim, Gyeonggi-do (KR); Chun-Sik Byun, Daejeon (KR); Jin-Heung Kim, Seoul (KR); Hui-Chan Kim, Daejeon (KR); Young-Jong Seo, Daejeon (KR)

(73) Assignee: Lotte Chemical Corporation, Seoul (KR)

( * ) Notice: Subject to any disclaimer, the term of this patent is extended or adjusted under 35 U.S.C. 154(b) by 0 days.

(21) Appl. No.: 13/890,538

(22) Filed: May 9, 2013

(65) Prior Publication Data
US 2014/0179952 A1   Jun. 26, 2014

(30) Foreign Application Priority Data

Dec. 26, 2012  (IN) ............................ 4012/DEL/2012

(51) Int. Cl.
| | | |
|---|---|---|
| *C07C 209/16* | (2006.01) | |
| *C07C 209/26* | (2006.01) | |
| *C07C 213/02* | (2006.01) | |
| *B01J 23/75* | (2006.01) | |
| *B01J 23/89* | (2006.01) | |
| *B01J 23/83* | (2006.01) | |
| *B01J 23/10* | (2006.01) | |

(52) U.S. Cl.
CPC ............ *B01J 23/894* (2013.01); *C07C 209/26* (2013.01); *C07C 213/02* (2013.01); *B01J 23/75* (2013.01); *B01J 23/83* (2013.01); *B01J 23/10* (2013.01)

USPC ........................... 564/479; 564/474; 564/480

(58) Field of Classification Search
None
See application file for complete search history.

(56) References Cited

U.S. PATENT DOCUMENTS

| | | |
|---|---|---|
| 4,086,189 A | 4/1978 | Honda et al. |
| 4,760,190 A | 7/1988 | Twigg |
| 5,932,769 A | 8/1999 | Vedage et al. |

FOREIGN PATENT DOCUMENTS

| | | | |
|---|---|---|---|
| EP | 0 211 552 A1 | 2/1987 | |
| GB | 1 459 632 A | 12/1976 | |
| JP | 2010-173970 A | * 8/2010 | ............ C07C 221/00 |

OTHER PUBLICATIONS

JPO English machine translation of the JP 2010/173970 A specification (Apr. 19, 2014).*
European Search Report for Application No. EP 13 16 3578 dated Sep. 24, 2013.

* cited by examiner

*Primary Examiner* — Brian J Davis
(74) *Attorney, Agent, or Firm* — Alston & Bird LLP

(57) ABSTRACT

The present invention relates to a catalyst for reductive amination-reaction, and uses thereof. The catalyst according to the present invention can show high amine conversion rate because it can maintain the catalytic activity even in the presence of moisture especially while maintaining the balance of dehydrogenation and hydrogenation reaction basically. Accordingly, the catalyst can be usefully used for preparing a polyetheramine compound through reductive amination-reaction not only in a continuous preparation process but also in a batch preparation process, irrespective of the existence of moisture.

10 Claims, No Drawings

CATALYST FOR REDUCTIVE AMINATION-REACTION AND USES THEREOF

CROSS REFERENCE TO RELATED APPLICATION

This application claims the benefit of and priority to Indian Patent Application No. 4012/DEL/2012, filed Dec. 26, 2012, the entire contents of which are hereby incorporated by reference.

BACKGROUND OF THE INVENTION (a) Field of the Invention

The present invention relates to a catalyst for reductive amination-reaction and uses thereof.

(b) Description of the Related Art

As known in the art to which the present invention pertains (hereinafter, 'the related art'), the reductive amination is one of the methods for obtaining an aliphatic alkane derivative to which amine groups are introduced through a catalytic amination-reaction of the aliphatic alkane derivative under a reductive condition and in the presence of hydrogen. Such reductive amination has been used for preparing various amine compounds such as polyetheramine.

The polyetheramine compound is a compound having at least one polyoxyalkylene group, it is being used in various ways such as a coating agent for wind power generator, an additive for epoxy coating, an additive for concrete, and the like, and it is generally prepared through reductive amination-reaction by using a compound such as a polyalkylene glycol and the like as a starting material.

In such reductive amination-reaction, a copper (Cu)-nickel (Ni) based catalyst has been used generally, and there are many attempts to increase the productivity by controlling the catalytic activity by using chromium (Cr), titanium (Ti), zirconium (Zr), zinc (Zn), molybdenum (Mo), and the like as an active component.

However, the reductive amination-reaction is accompanied by the processes of dehydrogenation, dehydration, and hydrogenation, the existing catalysts disclosed above have a problem that they lost the activity easily by moisture formed during the reductive amination-reaction, or a side-reaction proceeds by the excessive moisture, and the reaction efficiency decreases finally.

To make up for this problem, a method of eliminating moisture formed during the reaction from the reaction system by carrying out the reductive amination-reaction in a continuous process has been used. However, this continuous process has a disadvantage of that complex facilities are needed and overall production efficiency decreases.

Therefore, the development of new catalyst which has a balance of dehydrogenation and hydrogenation reaction and can maintain the catalytic activity even in a batch-type process for preparing a polyetheramine compound is urgently needed.

SUMMARY OF THE INVENTION

It is an aspect of the present invention to provide a catalyst for reductive amination-reaction which can maintain the catalytic activity and the balance of dehydrogenation and hydrogenation reaction even in the presence of moisture, and thus can show high amine conversion rate.

It is another aspect of the present invention to provide a method of preparing a polyetheramine compound using the catalyst.

According to one embodiment of the present invention, a catalyst for reductive amination-reaction including cobalt and yttrium as active components is provided.

The catalyst may include 1 to 30 parts by weight of yttrium oxide, based on 100 parts by weight of cobalt oxide.

Furthermore, the catalyst may further include palladium as an active component.

At this time, the catalyst may include 1 to 30 parts by weight of yttrium oxide, and 0.01 to 50 parts by weight of palladium oxide, based on 100 parts by weight of cobalt oxide.

And, the catalyst may further include a supporting material on which the active components are supported.

Meanwhile, according to another embodiment of the present invention, a method of preparing a polyetheramine compound including a step of bringing a polyether derivative into contact with an amine compound in the presence of the catalyst disclosed above and hydrogen is provided.

Here, the step may be carried out in the presence of 0.5 to 40 parts by weight of amine compound and 0.05 to 5 parts by weight of hydrogen, based on 100 parts by weight of the polyether derivative.

And, the step may be carried out at a temperature of 20° C. to 350° C. and under a pressure of 1 bar to 300 bar.

Furthermore, the polyether derivative may be a compound including 5 to 1000 carbon atoms and at least one functional group which can be substituted by an amine group.

Here, the functional group which can be substituted by an amine group may be one or more functional groups selected from the group consisting of a hydroxyl group, an aldehyde group, a ketone group, and an imino group.

Specifically, the polyether derivative may be a compound including a repeating unit of the following Chemical Formula 1:

[Chemical Formula 1]

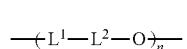

In Chemical Formula 1, $L^1$ and $L^2$ are independently a $C_1$-$C_{10}$ alkylene, a $C_2$-$C_{10}$ alkenylene, a $C_2$-$C_{10}$ alkynylene, a $C_3$-$C_{10}$ cycloalkylene, or a $C_6$-$C_{30}$ arylene, and n is an integer of 1 to 500.

And, the amine compound may be a primary amine compound or a secondary amine compound.

EFFECTS OF THE INVENTION

The catalyst according to the present invention can show high amine conversion rate because it can maintain a balance of dehydrogenation and hydrogenation reaction basically and the catalytic activity can be maintained even in the presence of moisture especially. Accordingly, the catalyst can be usefully used for preparing a polyetheramine compound through reductive amination-reaction not only in a continuous preparation process but also in a batch preparation process, irrespective of the existence of moisture.

DETAILED DESCRIPTION OF THE EMBODIMENTS

Hereinafter, the catalyst for reductive amination-reaction and the method of preparing a polyetheramine compound using the same according to embodiments of the present invention are explained, First of all, in the whole of the present specification, the term 'include' or 'comprise' means including any component (or constituent, or step) without any limitation, and it should not be understood as excluding or eliminating an addition of other components.

Hereinafter, catalysts for reductive amination-reaction according to embodiments of the present invention and a method of preparing a polyetheramine compound using the same are explained in more detail so that a person having ordinary skill in the related art can make this invention easily. However, the present invention may be realized in many different forms and it is not limited to the examples explained in this specification.

And, unless there is overt mention in the whole of the present specification, the technical terms used here are only for mentioning specific embodiments, and they do not intent to limit the present invention. Furthermore, the singular forms 'a', 'an', and 'the' used here include plural referents unless the context clearly dictates otherwise.

And, the term of 'include' used in the specification specifies specific characteristics, areas, essence, steps, motions, elements, or components, and it does not exclude existence or addition of the other characteristics, areas, essence, steps, motions, elements, or components.

Furthermore, 'reductive amination-reaction' or 'reductive amination' in the whole of the present specification means a series of reactions for forming an aliphatic alkane derivative to which amine groups are introduced through a catalytic amination-reaction of aliphatic alkane derivatives [for example, monohydric alcohol or polyhydric alcohol, alcohol amine, and derivatives thereof (for example, epoxide, ketone, alkylene imine, and the like)] under a reductive condition and in the presence of hydrogen.

For example of 'reductive amination-reaction', it may mean a series of reactions for forming an amine compound by dehydrogenating a compound including a terminal hydroxyl group so as to form an aldehyde compound, bringing the aldehyde compound into contact with a compound including an amine group so as to form an imine compound which is a reaction intermediate, and bringing the imine compound into contact with hydrogen so as to add hydrogen thereto, as the following reaction mechanism.

[Reaction Mechanism]

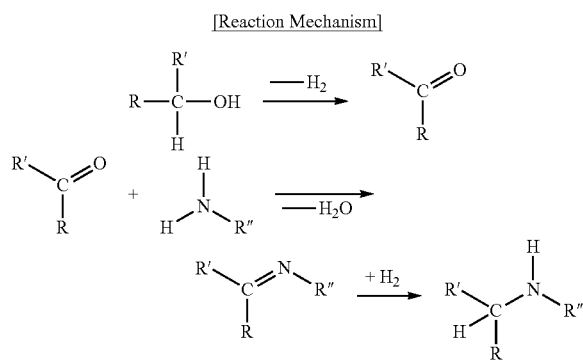

Furthermore, 'amine conversion rate' in the whole of the specification may mean the rate or the degree of that the aliphatic alkane derivative, the reactant of 'reductive amination', converts to the amine compound, the final product.

Meanwhile, in the course of studying the reductive amination, the present inventors recognized that when the reductive amination-reaction is carried out in the presence of the catalyst including cobalt (Co) and yttrium (Y) as active components, the catalytic activity can be maintained even in the presence of moisture especially while properly maintaining the balance of dehydrogenation and hydrogenation reaction that comes with the reaction. Furthermore, the present inventors also recognized that the catalytic reduction can smoothly occur in the catalyst activation process in addition to the effects disclosed above by using the catalyst including cobalt (Co), yttrium (Y), and palladium (Pd) as active components, and completed the present invention.

According to one embodiment of the present invention, a catalyst for reductive amination-reaction including cobalt (Co) and yttrium (Y) as active components is provided.

Generally, a copper (Cu)-nickel (Ni) based catalyst, a nickel (Ni)-rhenium (Re) based catalyst, a cobalt (Co)-Nickel (Ni)-copper (Cu) based catalyst, and the like have been used, and there have been many attempts to increase the catalytic activity by combining chromium (Cr), titanium (Ti), zirconium (Zr), zinc (Zn), molybdenum (Mo), and the like with the catalysts.

However, the existing catalysts disclosed above have a problem that they easily lost the activity by moisture formed during the reductive amination-reaction and the amine conversion rate decreases rapidly.

The catalyst according to one embodiment of the present invention, by comparison, includes cobalt (Co) and yttrium (Y) as active components, it has an advantage that the catalytic activity can be maintained even in the presence of moisture especially while properly maintaining the balance of dehydrogenation and hydrogenation reaction that comes with the reductive amination.

Such phenomenon may be related to the affinity of the active components included in the catalyst. Namely, the existing catalysts such as copper (Cu)-nickel (Ni) based catalyst and the like have stronger affinity to moisture than to the amine compound and hydrogen, the reactants of the reductive amination-reaction, and thus it comes to lost the catalytic activity by the moisture formed during the reaction, and the amine conversion rate decreases rapidly.

By comparison, the catalyst according to one embodiment of the present invention can maintain the catalytic activity and shows high amine conversion rate even though moisture is formed during the reaction, because cobalt (Co) and yttrium (Y) included in the catalyst have stronger affinity to the amine compound and hydrogen than to the moisture.

Furthermore, since the catalyst according to one embodiment of the present invention includes cobalt (Co) and yttrium (Y) as active components, it can maintain more stable balance in dehydrogenation and hydrogenation reaction that comes with the reductive amination-reaction due to their synergistic action.

According to one embodiment of the present invention, the catalyst includes cobalt (Co) and yttrium (Y) as active components, and preferably it may be a compound ($CoO-Y_2O_3$) including cobalt oxide (CoO) and yttrium oxide ($Y_2O_3$). The catalyst may have a composition of $CoO-Y_2O_3$ after calcination process, and may become a composition including (Cobalt metal)-(Yttrium metal) through a catalytic reduction condition. Such oxide type or metal type active components can be used as the catalyst in the reductive amination-reaction.

At this time, the catalyst may include 1 to 30 parts by weight of yttrium oxide; preferably 1 to 25 parts by weight of yttrium oxide; and more preferably 3 to 20 parts by weight of yttrium oxide, based on 100 parts by weight of cobalt oxide. Namely, it is advantageous to include cobalt oxide and yttrium oxide in the amount disclosed above so as to realize at least minimum effect due to the synergistic action of cobalt and yttrium, by considering the degree of improvement of the catalytic activity according to the weight ratio of cobalt and yttrium.

Meanwhile, according to another embodiment of the present invention, the catalyst may further include palladium (Pd) as an active component.

Since palladium (Pd) makes the catalytic reduction occur more smoothly during the activation process of the catalyst due to the synergistic action of cobalt and yttrium though it is hardly affected by moisture formed during the reductive amination-reaction, it can improve the amine conversion rate finally.

Palladium (Pd) may be included in a form of palladium oxide in the catalyst ($CoO-Y_2O_3-PdO$).

Especially, according to the present invention, the catalyst may include 1 to 30 parts by weight of yttrium oxide, and 0.01 to 50 parts by weight of palladium oxide; preferably 0.01 to 45 parts by weight of palladium oxide; and more preferably 0.1 to 45 parts by weight of palladium oxide, based on 100 parts by weight of cobalt oxide. Namely, it is advantageous to include the active components in the amount disclosed above, by considering the degree of improvement of the catalytic activity according to their weight ratio while realizing at least minimum effect due to the synergistic action of cobalt, yttrium, and palladium.

Meanwhile, the catalyst for reductive amination-reaction according to the present invention may further include a supporting material.

Namely, the catalyst may be a supported catalyst that the active components including cobalt and yttrium are supported on a certain supporting material, and the catalyst may further include palladium as an active component. Like this, the supported catalyst that the active components are supported on the supporting material can secure the specific area of the active components, and an equivalent effect can be obtained even by using relatively small quantity of the active components.

Here, any usual material known in the related art can be used as the supporting material, if it does not have a bad influence on the activity of the active components. According to one embodiment of the present invention, however, the supporting material may be $SiO_2$, $Al_2O_3$, $MgO$, $MgCl_2$, $CaCl_2$, $ZrO_2$, $TiO_2$, $B_2O_3$, $CaO$, $ZnO$, $BaO$, $ThO_2$, $SiO_2-Al_2O_3$, $SiO_2-MgO$, $SiO_2-TiO_2$, $SiO_2-V_2O_5$, $SiO_2-CrO_2$, $SiO_2-TiO_2-MgO$, bauxite, zeolite, starch, cyclodextrine, or a synthetic polymer.

As a method of supporting the active components disclosed above onto the supporting material, usual supporting methods known in the related art such as a method of supporting the active components onto a dehydrated supporting material directly; a method of mixing the active components and a supporting material, supporting the active components by a precipitation method, and calcining the same; and the like may be used.

At this time, the content of the active components supported on the supporting material is not limited particularly, because it can be determined by considering the range of content which can show a minimum activity, and the effect of reducing the amount of the active components according to the use of the supporting material. The active components, however, may be included in an amount of 1 or more parts by weight, preferably 1 to 200 parts by weight, and more preferably 10 to 150 parts by weight, based on 100 parts by weight of the supporting material. Here, the case of including 100 parts by weight of the active components based on 100 parts by weight of the supporting material can be expressed as 'the active components are supported by 50 weight %'.

Above this, the catalyst may further include a co-catalyst compound for improving the activity of the active components disclosed above. The co-catalyst compound may be supported on the supporting material disclosed above along with the active components, and any existing co-catalyst compound known in the related art may be used without particular limitation.

Meanwhile, since the catalyst can be prepared according to a usual method known in the related art, specific features of the preparation method are also not limited particularly.

According to the present invention, however, the catalyst including the active components disclosed above may be prepared through a precipitation method. As an unlimited example, a catalyst according to one embodiment may be prepared by dissolving cobalt nitrate and yttrium nitrate in water, adding a sodium carbonate solution thereto so as to precipitate a salt including cobalt oxide and yttrium oxide, and washing, drying, and calcining the precipitated salt. Further, a catalyst according to another embodiment may be prepared by adding an aqueous solution of palladium nitrate to the calcined catalyst prepared above and mixing the same, and drying the same at high temperature.

Such catalyst of the present invention can be used for preparing an amine-capped aliphatic alkane derivative through the reductive amination of aliphatic alkane derivatives such as monohydric alcohol or polyhydric alcohol, alcohol amine, and derivatives thereof (for example, epoxide, ketone, alkylene imine, and the like). Preferably, the catalyst can be usefully used for preparing a polyetheramine compound through the reductive amination of a polyether derivative.

Meanwhile, according to still another embodiment of the present invention, a method of preparing a polyetheramine compound including a step of bringing a polyether derivative into contact with an amine compound, in the presence of the catalyst for reductive amination-reaction disclosed above and hydrogen is provided.

Namely, according to the present invention, a method of preparing an amine-capped polyether derivative by reductive amination-reaction of a polyether derivative in the presence of the catalyst disclosed above is provided.

Particularly, as the method of preparing polyetheramine compound according to the present invention is carried out in the presence of the catalyst disclosed above, it has an advantage of that the activity of catalyst can be maintained though water ($H_2O$) is formed during the reaction and the polyetheramine compound can be prepared with high amine conversion rate. Accordingly, the preparation method according to the present invention can be applied not only to a continuous process but also to a batch process, and it is possible to prepare the polyetheramine compound by using more simplified production facilities. Furthermore, the preparation method can provide high selectivity for the primary amine compound which is industrially more useful.

Meanwhile, according to the present invention, the preparation method can be carried out through a series of reactions including a reaction for forming an aldehyde compound by dehydrogenating the polyether derivative; a reaction for forming an imine compound by bringing the aldehyde compound into contact with an amine compound; and a hydrogenating reaction by bringing the imine compound into contact with hydrogen. In the preparation method, however, each reaction disclosed above may be carried out separately or may be carried out through a series of continuous reactions undifferentiated in process condition and process efficiency. Namely, the preparation method may be carried out through a series of reductive amination-reactions which bring a polyether derivative into contact with an amine compound in the presence of the catalyst disclosed above and hydrogen.

In the present invention, a preferable material (i.e. reactant) for the reductive amination using the catalyst disclosed above is a polyether derivative, and it can provide a compound capped by at least one amine group (i.e. polyetheramine compound) finally.

Specifically, the polyether derivative may be a polyether based compound having at least one functional group which can be substituted by an amine group, and it may be a compound including 5 to 1000 carbon atoms preferably.

Here, the functional group which can be substituted by the amine group may be one or more functional groups selected from the group consisting of a hydroxyl group, an aldehyde group, a ketone group, and an imino group.

Therefore, in the present invention, any polyether derivative satisfying the conditions disclosed above can be used as the reactant without particular limitation. However, preferably, the polyether derivative may be a compound including a functional group which can be substituted by the amine group, and a repeating unit of Chemical Formula 1:

[Chemical Formula 1]

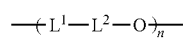

In Chemical Formula 1, $L^1$ and $L^2$ are independently a $C_1$-$C_{10}$ alkylene, a $C_2$-$C_{10}$ alkenylene, a $C_2$-$C_{10}$ alkynylene, a $C_3$-$C_{10}$ cycloalkylene, or a $C_6$-$C_{30}$ arylene, and n is an integer of 1 to 500.

Here, the 'alkylene' means a secondary functional group derived from a linear or branched alkane; 'alkenylene' means a secondary functional group derived from a linear or branched alkene; 'alkynylene' means a secondary functional group derived from a linear or branched alkyne; 'cycloalkylene' means a secondary functional group derived from a cycloalkane; and 'arylene' means a secondary functional group derived from an arene.

According to one embodiment of the present invention, the polyether derivative may be an alcohol (ethyl alcohol, propyl alcohol, butyl alcohol, aliphatic alcohol, alkylphenyl alcohol, and the like) including the repeating unit of Chemical Formula 1, a glycol (polyethylene glycol, polypropylene glycol, polytetramethylene ether glycol, and the like) including the repeating unit of Chemical Formula 1, a triol including the repeating unit of Chemical Formula 1, an aldehyde compound including the repeating unit of Chemical Formula 1, a ketone compound including the repeating unit of Chemical Formula 1, or an imino compound including the repeating unit of Chemical Formula 1.

And, the compound including the repeating unit of Chemical Formula 1 may be a block polymer or a random polymer including the repeating unit. For example, the polyether derivative may include a copolymer such as polypropylene glycol-polyethylene glycol-polypropylene glycol and the like.

Meanwhile, according to another embodiment of the present invention, the polyether derivative may be a polyoxyalkylene compound represented by the following Chemical Formula 2:

[Chemical Formula 2]

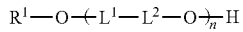

In Chemical Formula 2, $L^1$ and $L^2$ are independently a $C_1$-$C_{10}$ alkylene, a $C_2$-$C_{10}$ alkenylene, a $C_2$-$C_{10}$ alkynylene, a $C_3$-$C_{10}$ cycloalkylene, or a $C_6$-$C_{30}$ arylene, $R^1$ is hydrogen, a $C_1$-$C_{18}$ alkyl group, a un-substituted $C_6$-$C_{30}$ aryl group, or a $C_6$-$C_{30}$ aryl group substituted by a $C_1$-$C_{18}$ alkyl group, and n is an integer of 1 to 500.

And, according to still another embodiment of the present invention, the polyether derivative may be a polyoxyalkylene compound represented by the following Chemical Formula 3:

[Chemical Formula 3]

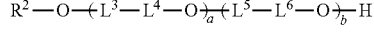

In Chemical Formula 3, $L^3$ to $L^6$ are independently a $C_1$-$C_{10}$ alkylene, a $C_2$-$C_{10}$ alkenylene, a $C_2$-$C_{10}$ alkynylene, a $C_3$-$C_{10}$ cycloalkylene, or a $C_6$-$C_{30}$ arylene, $R^2$ is hydrogen, a $C_1$-$C_{18}$ alkyl group, a un-substituted $C_6$-$C_{30}$ aryl group, or a $C_6$-$C_{30}$ aryl group substituted by a $C_1$-$C_{18}$ alkyl group, and a and b are independently an integer of 1 to 500.

And, according to still another embodiment of the present invention, the polyether derivative may be a polyoxyalkylene compound represented by the following Chemical Formula 4:

[Chemical Formula 4]

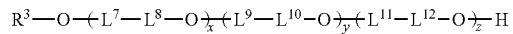

In Chemical Formula 4, $L^7$ to $L^{12}$ are independently a $C_1$-$C_{10}$ alkylene, a $C_2$-$C_{10}$ alkenylene, a $C_2$-$C_{10}$ alkynylene, a $C_3$-$C_{10}$ cycloalkylene, or a $C_6$-$C_{30}$ arylene, $R^3$ is hydrogen, a $C_1$-$C_{18}$ alkyl group, a un-substituted $C_6$-$C_{30}$ aryl group, or a $C_6$-$C_{30}$ aryl group substituted by a $C_1$-$C_{18}$ alkyl group, and y is an integer of 2 to 500, and (x+z) is an integer of 2 to 100.

The compounds of Chemical Formula 2 to Chemical Formula 4 disclosed above are polyoxyalkylene compounds including at least one hydroxyl end group, and they can be used as an example of the reactant in the reductive amination-reaction according to the present invention.

Meanwhile, in the method of preparing the polyetheramine compound according to the present invention, the polyether derivative reacts with one or more amine compounds.

As the amine compound, usual compounds including an amine group may be used without particular limitation, and preferably, a primary amine compound or a secondary amine compound may be used. More preferably, the amine compound may be one or more compounds selected from the group consisting of ammonia, methylamine, ethylamine, propylamine, butylamine, ethylenediamine, aniline, piperazine, aminoethylpiperazine, diethylenetriamine, triethylenetetramine, tetraethylenepentamine, pentaethylenehexamine, diethylamine, dipropylamine, dibutylamine, isopropylamine, diisopropylamine, diisopropanolamine, ethanolamine, diethanolamine, and diisobutyleneamine.

In the step of bringing the polyether derivative into contact with the amine compound, the weight ratio of the reactant is not limited particularly because it can be determined within the range in which a series of reactions can be carried out sufficiently by considering the reaction efficiency. According to the present invention, however, it may be advantageous in terms of the improvement of the reaction efficiency that the step is carried out in the presence of 0.5 to 40 parts by weight, preferably 1 to 40 parts by weight, more preferably 1 to 35 parts by weight of the amine compound; and 0.05 to 5 parts by weight, preferably 0.1 to 3 parts by weight, more preferably 0.1 to 2 parts by weight of hydrogen; based on 100 parts by weight of the polyether derivative.

And, it may be advantageous in terms of the improvement of the reaction efficiency that the step is carried out at the temperature of 20° C. to 350° C. and under the pressure of 1 bar to 300 bar; preferably at the temperature of 20° C. to 300° C. and under the pressure of 1 bar to 250 bar; and more preferably at the temperature of 20° C. to 250° C. and under the pressure of 1 bar to 220 bar.

Meanwhile, in addition to the steps disclosed above, the preparation method of polyetheramine compound according to the present invention may further include a usual step known in the related art before or after each step disclosed above.

Hereinafter, preferable examples are provided for understanding the present invention. However, the following examples are only for illustrating the present invention, and the present invention is not determined to or by them.

First, the catalysts of Examples and Comparative were prepared by the following methods (Examples 1-4 and Comparative Examples 1-2), and the polyetheramine compounds were prepared by using each catalyst (Examples 5-9 and Comparative Examples 3-4).

And, the results of Examples and Comparative Examples are summarized in the following Table 1.

At this time, 'amine conversion rate' means the rate (weight ratio) that the polyether derivative the starting material is converted into the polyetheramine compound, and the weight of the polyetheramine compound was measured by the titration method according to Total Amine Value measurement (ASTM D2074).

And, 'primary amine selectivity' means the rate (weight ratio) of the primary amine compound in the product, and it was measured by the titration method according to Primary Amine Value measurement (ASTM D2074).

EXAMPLE 1

Preparation of $CoO$—$Y_2O_3$ Catalyst

At room temperature, about 44.034 g of cobalt nitrate and about 0.525 g of yttrium nitrate were dissolved in about 400 g of water, and the precipitation method was carried out by injecting 15 wt % aqueous solution of sodium carbonate with a speed of about 0.08 ml/s.

After about 1 hour passed, the formed salt was washed and filtered numerous times by using about 500 ml of distilled water, and it was dried at about 110° C. for about 15 hours.

The $CoO$—$Y_2O_3$ catalyst (including about 6.03 parts by weight of $Y_2O_3$, based on 100 parts by weight of CoO) was obtained by the method of putting the salt dried like above into a furnace and raising the furnace temperature up to about 600° C. with a heating rate of about 300° C./hr, and calcining the salt for about 4 hours at about 600° C. under ambient atmosphere.

EXAMPLE 2

Preparation of $CoO$—$Y_2O_3$—$PdO$ Catalyst

At room temperature, about 44.034 g of cobalt nitrate and about 0.525 g of yttrium nitrate were dissolved in about 400 g of water, and the precipitation method was carried out by injecting 15 wt % aqueous solution of sodium carbonate with a speed of about 0.08 ml/s.

After about 1 hour passed, the formed salt was washed and filtered numerous times by using about 500 ml of distilled water, and it was dried at about 110° C. for about 15 hours.

The salt dried like above was put into a furnace, and calcined for about 4 hours at about 600° C. under ambient atmosphere after raising the furnace temperature up to about 600° C. with a heating rate of about 300° C./hr.

The $CoO$—$Y_2O_3$—$PdO$ catalyst (including about 6.03 parts by weight of $Y_2O_3$ and about 0.13 parts by weight of PdO, based on 100 parts by weight of CoO) was obtained by the method of adding 20 ml of an aqueous solution in which about 0.028 g of palladium nitrate was dissolved to the calcined salt and mixing together, and drying the same at about 110° C. for about 15 hours.

EXAMPLE 3

Preparation of $CoO$—$Y_2O_3$—$PdO$ Catalyst

At room temperature, about 44.034 g of cobalt nitrate and about 0.525 g of yttrium nitrate were dissolved in about 400 g of water, and the precipitation method was carried out by injecting 15 wt % aqueous solution of sodium carbonate with a speed of about 0.08 ml/s.

After about 1 hour passed, the formed salt was washed and filtered numerous times by using about 500 ml of distilled water, and it was dried at about 110° C. for about 15 hours.

The salt dried like above was put into a furnace, and calcined for about 4 hours at about 600° C. under ambient atmosphere after raising the furnace temperature up to about 600° C. with a heating rate of about 300° C./hr.

The $CoO$—$Y_2O_3$—$PdO$ catalyst (including about 6.03 parts by weight of $Y_2O_3$ and about 0.26 parts by weight of PdO, based on 100 parts by weight of CoO) was obtained by the method of adding 20 ml of an aqueous solution in which about 0.056 g of palladium nitrate was dissolved to the calcined salt and mixing together, and drying the same at about 110° C. for about 15 hours.

EXAMPLE 4

Preparation of $CoO$—$Y_2O_3$—$PdO$ Supported Catalyst

At room temperature, about 22.017 g of cobalt nitrate and about 0.2625 g of yttrium nitrate were dissolved in about 200 g of water, and about 100 g of water including about 6 g of $Al_2O_3$ (produced by Aldrich) as a supporting material was added thereto, and the precipitation method was carried out by injecting 15 wt % aqueous solution of sodium carbonate with a speed of about 0.08 ml/s.

After about 1 hour passed, the formed salt was washed and filtered numerous times by using about 500 ml of distilled water, and it was dried at about 110° C. for about 15 hours.

The salt dried like above was put into a furnace, and calcined for about 4 hours at about 600° C. under ambient atmosphere after raising the furnace temperature up to about 600° C. with a heating rate of about 300° C./hr.

The CoO—Y₂O₃—PdO catalyst (including about 6.03 parts by weight of Y₂O₃ and about 0.13 parts by weight of PdO, based on 100 parts by weight of CoO) was obtained by the method of adding 20 ml of an aqueous solution in which about 0.014 g of palladium nitrate was dissolved to the calcined salt and mixing together, and drying the same at about 110° C. for about 15 hours.

EXAMPLE 5

Preparation of Polyetheramine Compound

About 3.5 g of the catalyst according to Example 1 and about 70 g of polypropylene glycol (produced by Aldrich, product name: PPG-1000, number average molecular weight (Mn): about 1,000) represented by the following Chemical Formula were put into a batch type reactor of 200 ml capacity.

[Chemical Formula]

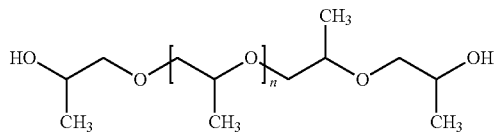

Subsequently, oxygen in the reactor was eliminated by 5 times nitrogen purge, and about 50 bar of hydrogen was injected thereinto at room temperature. After then, the catalyst activation was carried out for about 1 hour after raising the temperature of the reactor up to about 250° C., and subsequently hydrogen in the reactor was vented out after cooling the temperature of the reactor to about 80° C.

And, after cooling the temperature of the reactor to about 40° C., about 23.8 g of ammonia of about −20° C. was injected in company with hydrogen so as to make the pressure in the reactor be 50 bar (about 34.0 parts by weight of ammonia and about 0.7 parts by weight of hydrogen, based on 100 parts by weight of PPG-1000). After then, about 28.7 g of the polyetheramine compound (amine conversion rate: about 41.0%, primary amine selectivity: about 99.1%) was obtained by the method of raising the temperature of the reactor up to 220° C. and reacting the contents under the pressure of about 200 bar for about 5 hours.

EXAMPLE 6

Preparation of Polyetheramine Compound

About 3.5 g of the catalyst according to Example 2 and about 70 g of polypropylene glycol (product name: PPG-1000, produced by Aldrich) same as Example 5 were put into a batch type reactor of 200 ml capacity.

Subsequently, oxygen in the reactor was eliminated by 5 times nitrogen purge, and about 50 bar of hydrogen was injected thereinto at room temperature. After then, the catalyst activation was carried out for about 1 hour after raising the temperature of the reactor up to about 250° C., and subsequently hydrogen in the reactor was vented out after cooling the temperature of the reactor to about 80° C.

And, after cooling the temperature of the reactor to about 40° C., about 18.0 g of ammonia of about −20° C. was injected in company with hydrogen so as to make the pressure in the reactor be 50 bar (about 25.7 parts by weight of ammonia and about 0.7 parts by weight of hydrogen, based on 100 parts by weight of PPG-1000). After then, about 69.5 g of the polyetheramine compound (amine conversion rate: about 99.2%, primary amine selectivity: about 99.6%) was obtained by the method of raising the temperature of the reactor up to 220° C. and reacting the contents under the pressure of about 180 bar for about 5 hours.

EXAMPLE 7

Preparation of Polyetheramine Compound

About 69.65 g of the polyetheramine compound (amine conversion rate: about 99.5%, primary amine selectivity: about 99.9%) was obtained substantially according to the same conditions and method as in Example 5, except that the amount of ammonia used was changed to 23.8 g (about 34 parts by weight of ammonia and about 0.7 parts by weight of hydrogen, based on 100 parts by weight of PPG-1000) and the temperature of the reactor was raised up to 220° C. and reacting the contents under the pressure of about 200 bar for about 5 hours.

EXAMPLE 8

Preparation of Polyetheramine Compound

About 3.5 g of the catalyst according to Example 3 and about 70 g of polypropylene glycol (product name: PPG-1000, produced by Aldrich) same as Example 5 were put into a batch type reactor of 200 ml capacity.

Subsequently, oxygen in the reactor was eliminated by 5 times nitrogen purge, and about 50 bar of hydrogen was injected thereinto at room temperature. After then, the catalyst activation was carried out for about 1 hour after raising the temperature of the reactor up to about 250° C., and subsequently hydrogen in the reactor was vented out after cooling the temperature of the reactor to about 80° C.

And, after cooling the temperature of the reactor to about 40° C., about 18.0 g of ammonia of about −20° C. was injected in company with hydrogen so as to make the pressure in the reactor be 50 bar (about 25.7 parts by weight of ammonia and about 0.7 parts by weight of hydrogen, based on 100 parts by weight of PPG-1000). After then, about 69.7 g of the polyetheramine compound (amine conversion rate: about 99.5%, primary amine selectivity: about 99.9%) was obtained by the method of raising the temperature of the reactor up to 220° C. and reacting the contents under the pressure of about 180 bar for about 5 hours.

EXAMPLE 9

Preparation of Polyetheramine Compound

About 3.5 g of the catalyst according to Example 4 and about 70 g of polypropylene glycol (product name: PPG-1000, produced by Aldrich) same as Example 5 were put into a batch type reactor of 200 ml capacity.

Subsequently, oxygen in the reactor was eliminated by 5 times nitrogen purge, and about 50 bar of hydrogen was injected thereinto at room temperature. After then, the catalyst activation was carried out for about 1 hour after raising the temperature of the reactor up to about 250° C., and subsequently hydrogen in the reactor was vented out after cooling the temperature of the reactor to about 80° C.

And, after cooling the temperature of the reactor to about 40° C., about 23.8 g of ammonia of about −20° C. was injected in company with hydrogen so as to make the pressure in the reactor be 50 bar (about 34 parts by weight of ammonia and about 0.7 parts by weight of hydrogen, based on 100 parts by weight of PPG-1000). After then, about 69.65 g of the polyetheramine compound (amine conversion rate: about 99.5%, primary amine selectivity: about 99.5%) was obtained by the method of raising the temperature of the reactor up to 220° C. and reacting the contents under the pressure of about 200 bar for about 5 hours.

COMPARATIVE EXAMPLE 1

Preparation of CoO Catalyst

At room temperature, about 44.034 g of cobalt nitrate was dissolved in about 400 g of water, and the precipitation method was carried out by injecting 15 wt % aqueous solution of sodium carbonate with a speed of about 0.08 ml/s.

After about 1 hour passed, the formed salt was washed and filtered numerous times by using about 500 ml of distilled water, and it was dried at about 110° C. for about 15 hours.

The CoO catalyst was obtained by the method of putting the salt dried like above into a furnace, raising the furnace temperature up to about 600° C. with a heating rate of about 300° C./hr, and calcining the salt for about 4 hours at about 600° C. under ambient atmosphere.

COMPARATIVE EXAMPLE 2

Preparation of CuO—NiO/$Al_2O_3$ Catalyst

At room temperature, about 9.437 g of copper nitrate and about 3.893 g of nickel nitrate were dissolved in about 400 g of water, and about 5 g of aluminum oxide ($Al_2O_3$) was inserted thereinto. The precipitation method was carried out by injecting 15 wt % aqueous solution of sodium carbonate with a speed of about 0.03 ml/s.

After about 1 hour passed, the formed salt was washed and filtered numerous times by using about 500 ml of distilled water, and it was dried at about 110° C. for about 15 hours.

The CuO—NiO/$Al_2O_3$ catalyst (including about 20 parts by weight of NiO, based on 100 parts by weight of CuO) was obtained by the method of putting the salt dried like above into a furnace, raising the furnace temperature up to about 450° C. with a heating rate of about 300° C./hr, and calcining the salt for about 4 hours at about 450° C. under ambient atmosphere.

COMPARATIVE EXAMPLE 3

Preparation of Polyetheramine Compound

About 3.5 g of the catalyst according to Comparative Example 1 and about 70 g of polypropylene glycol (product name: PPG-1000, produced by Aldrich) same as Example 5 were put into a batch type reactor of 200 ml capacity.

Subsequently, oxygen in the reactor was eliminated by 5 times nitrogen purge, and about 50 bar of hydrogen was injected thereinto at room temperature. After then, the catalyst activation was carried out for about 1 hour after raising the temperature of the reactor up to about 250° C., and subsequently hydrogen in the reactor was vented out after cooling the temperature of the reactor to about 80° C.

And, after cooling the temperature of the reactor to about 40° C., about 23.8 g of ammonia of about −20° C. was injected in company with hydrogen so as to make the pressure in the reactor be 50 bar (about 34 parts by weight of ammonia and about 0.7 parts by weight of hydrogen, based on 100 parts by weight of PPG-1000). After then, about 10.64 g of the polyetheramine compound (amine conversion rate: about 15.2%, primary amine selectivity: about 94.0%) was obtained by the method of raising the temperature of the reactor up to 220° C. and reacting the contents under the pressure of about 200 bar for about 5 hours.

COMPARATIVE EXAMPLE 4

Preparation of Polyetheramine Compound

About 3.5 g of the catalyst according to Comparative Example 2 and about 70 g of polypropylene glycol (product name: PPG-1000, produced by Aldrich) same as Example 5 were put into a batch type reactor of 200 ml capacity.

Subsequently, oxygen in the reactor was eliminated by 5 times nitrogen purge, and about 50 bar of hydrogen was injected thereinto at room temperature. After then, the catalyst activation was carried out for about 1 hour after raising the temperature of the reactor up to about 250° C., and subsequently hydrogen in the reactor was vented out after cooling the temperature of the reactor to about 80° C.

And, after cooling the temperature of the reactor to about 40° C., about 23.8 g of ammonia of about −20° C. was injected in company with hydrogen so as to make the pressure in the reactor be 50 bar (about 34 parts by weight of ammonia and about 0.7 parts by weight of hydrogen, based on 100 parts by weight of PPG-1000). After then, about 4.12 g of the polyetheramine compound (amine conversion rate: about 5.9%, primary amine selectivity: about 2%) was obtained by the method of raising the temperature of the reactor up to 220° C. and reacting the contents under the pressure of about 200 bar for about 5 hours.

TABLE 1

| | Catalyst | Reaction temperature (° C.) | Reaction pressure (bar) | Amount of ammonia used (g) | Amine conversion rate (%) | Primary amine selectivity (%) |
|---|---|---|---|---|---|---|
| Example 5 | Example 1 (CoO—$Y_2O_3$) | 220 | 200 | 23.8 | 41.0 | 99.1 |
| Example 6 | Example 2 (CoO—$Y_2O_3$—PdO) (PdO 0.13 PBW*) | 220 | 180 | 18.0 | 99.2 | 99.6 |
| Example 7 | Example 2 (CoO—$Y_2O_3$—PdO) (PdO 0.13 PBW) | 220 | 180 | 23.8 | 99.5 | 99.9 |
| Example 8 | Example 3 (CoO—$Y_2O_3$—PdO) (PdO 0.26 PBW) | 220 | 180 | 18.0 | 99.5 | 99.9 |

TABLE 1-continued

| | Catalyst | Reaction temperature (° C.) | Reaction pressure (bar) | Amount of ammonia used (g) | Amine conversion rate (%) | Primary amine selectivity (%) |
|---|---|---|---|---|---|---|
| Example 9 | Example 4 (CoO—$Y_2O_3$—PdO, supported) | 220 | 200 | 23.8 | 99.5 | 99.5 |
| Comparative Example 3 | Comparative Example 1 (CoO) | 220 | 200 | 23.8 | 15.2 | 94.0 |
| Comparative Example 4 | Comparative Example 2 (CuO—NiO/$Al_2O_3$) | 220 | 200 | 23.8 | 5.9 | 2.0 |

*PBW: parts by weight

As known in Examples and Comparative Examples, the preparation methods of Comparative Examples 3 and 4 using the catalysts of Comparative Examples 1 and 2 show low amine conversion rate below 20%. Namely, it is recognized that the existing catalysts like Comparative Examples 3 and 4 decrease in the catalytic activity rapidly if there is moisture in the reactor and overall efficiency of the amination-reaction decreases.

In comparison, the preparation methods of Examples 5-9 using the catalysts show not only high amine conversion rate but also high selectivity in the primary amine compound which is industrially more useful.

And, as known in Examples 6 and 7, it is recognized that the amine conversion rate and the primary amine selectivity can be improved by increasing the amount of ammonia used within preferable range.

Furthermore, it is recognized that the supported catalyst including the supporting material like Example 9 can show the amine conversion rate being equivalent to other Examples, even though the content of the active components are decreased to nearly half.

What is claimed is:

1. A method of preparing a polyetheramine compound, including a step of bringing a polyether derivative into contact with an amine compound, in the presence of hydrogen and a catalyst for reductive amination-reaction including cobalt and yttrium as active components, wherein the polyether derivative is a polyoxyalkylene compound represented by the following Chemical Formula:

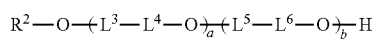

wherein,
X is a single bond or -($L^5$-$L^6$-O)$_c$—,
$L^1$ to $L^6$ are independently a $C_1$-$C_{10}$ alkylene, a $C_2$-$C_{10}$ alkenylene, a $C_2$-$C_{10}$ alkynylene, a $C_3$-$C_{10}$ cycloalkylene, or a $C_6$-$C_{10}$ arylene, $R^1$ is hydrogen, a $C_1$-$C_{18}$ alkyl group, an un-substituted $C_6$-$C_{30}$ aryl group, or a $C_6$-$C_{30}$ aryl group substituted by a $C_1$-$C_{18}$ alkyl group,
a and b are independently an integer of 1 to 500, and
c is an integer of 2 to 500.

2. The method according to claim 1, wherein the step is carried out in the presence of 0.5 to 40 parts by weight of amine compound and 0.05 to 5 parts by weight of hydrogen, based on 100 parts by weight of polyether derivative.

3. The method according to claim 1, wherein the step is carried out at a temperature of 20° C. to 350° C. and under a pressure of 1 bar to 300 bar.

4. The method according to claim 1, wherein the amine compound is a primary amine compound or a secondary amine compound.

5. The method according to claim 1, wherein the amine compound is one or more compounds selected from the group consisting of ammonia, methylamine, ethylamine, propylamine, butylamine, ethylenediamine, aniline, piperazine, aminoethylpiperazine, diethylenetriamine, triethylenetetramine, tetraethylenepentamine, pentaethylenehexamine, diethylamine, dipropylamine, dibutylamine, isopropyl amine, diisopropylamine, diisopropanolamine, ethanolamine, diethanolamine, and diisobutyleneamine.

6. The method according to claim 1, wherein the catalyst includes 1 to 30 parts by weight of yttrium oxide, based on 100 parts by weight of cobalt oxide.

7. The method according to claim 1, wherein the catalyst further includes a supporting material on which the active components are supported.

8. The method according to claim 1, wherein the catalyst further includes palladium as an active component.

9. The method according to claim 8, wherein the catalyst includes 1 to 30 parts by weight of yttrium oxide and 0.01 to 50 parts by weight of palladium oxide, based on 100 parts by weight of cobalt oxide.

10. The method according to claim 8, wherein the catalyst further includes a supporting material on which the active components are supported.

* * * * *

UNITED STATES PATENT AND TRADEMARK OFFICE
CERTIFICATE OF CORRECTION

PATENT NO. : 8,895,784 B2
APPLICATION NO. : 13/890538
DATED : November 25, 2014
INVENTOR(S) : Kim et al.

Page 1 of 1

It is certified that error appears in the above-identified patent and that said Letters Patent is hereby corrected as shown below:

In the claims:

Column 15,
Lines 47-50, the formula should appear as follows:

Line 55, "$C_6$-$C_{10}$" should read --$C_6$-$C_{30}$--

Signed and Sealed this
Nineteenth Day of May, 2015

Michelle K. Lee
*Director of the United States Patent and Trademark Office*